United States Patent
Chand et al.

(10) Patent No.: US 6,518,299 B1
(45) Date of Patent: Feb. 11, 2003

(54) SUBSTITUTED PYRROLIDINE COMPOUNDS USEFUL AS NEURAMINIDASE INHIBITORS

(75) Inventors: Pooran Chand, Birmingham, AL (US); Pravin L. Kotian, Birmingham, AL (US); Yarlagadda S. Babu, Birmingham, AL (US); John A. Montgomery, Birmingham, AL (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 0 days.

(21) Appl. No.: 09/692,518

(22) Filed: Oct. 20, 2000

(51) Int. Cl.[7] .................. A61K 31/40; C07D 207/16
(52) U.S. Cl. ........................ 514/423; 548/531
(58) Field of Search ................ 548/531; 514/423

(56) References Cited

U.S. PATENT DOCUMENTS 5,676,978 A * 10/1997 Teicher et al. ............. 424/649

FOREIGN PATENT DOCUMENTS

| WO | WO 98/17647 | 4/1998 |
| WO | WO 99/54299 | 10/1999 |

OTHER PUBLICATIONS

Yamazaki et al., CA 125:67270, 1996.*

* cited by examiner

Primary Examiner—Laura L. Stockton
(74) Attorney, Agent, or Firm—Connolly Bove Lodge & Hutz, LLP

(57) ABSTRACT

Certain substituted pyrrolidine compounds, pharmaceutically acceptable salts thereof, and their method of preparation are disclosed as well as use as influenza virus neuraminidase inhibitors.

1 Claim, No Drawings

SUBSTITUTED PYRROLIDINE COMPOUNDS USEFUL AS NEURAMINIDASE INHIBITORS

TECHNICAL FIELD

This invention relates to novel substituted pyrrolidine compounds and derivatives thereof useful as neuraminidase inhibitors, to pharmaceutical compositions containing said compounds useful for the prevention, treatment or amelioration of viral, bacterial and other infections, and to methods of using said compounds. The present invention is also concerned with novel intermediates or precursors for producing the novel substituted pyrrolidine compounds of the present invention.

BACKGROUND OF THE INVENTION

Despite the wealth of information available, influenza go remains a potentially devastating disease of man, lower mammals, and birds. No effective vaccine exists and no cure is available once the infection has been initiated.

Influenza viruses consist of eight pieces of single stranded is RNA, packaged in orderly fashion within the virion. Each piece codes for one of the major viral proteins. The replication complex is enclosed with a membrane composed of matrix protein associated with a lipid bilayer. Embedded in the lipid bilayer are two surface glycoprotein spikes, hemagglutinin (HA) and the enzyme neuraminidase (NA). All of the viral genes have been cloned and the three-dimensional structures of the surface glycoproteins have been determined.

Influenza viruses continually undergo antigenic variation in the two surface antigens, HA and NA, toward which neutralizing antibodies are directed. For this reason, vaccines and a subject's natural immune system have not been very effective. Attention is now being directed to finding other potential antiviral agents acting at other sites of the virion. This invention is directed to novel compounds which are useful in inhibiting the viral surface enzyme NA.

Furthermore, many other organisms carry NA. Many of these NA-possessing organisms are also major pathogens of man and/or mammals, including Vibraeo cholerae, Clostridium perfringes, Streptococcus pneumonia, Arthrobacter sialophilas, and other viruses, such as parainfluenza virus, mumps virus, Newcastle disease virus, fowl plague virus, and Sendai virus. Compounds of this invention are also directed to inhibiting NA of these organisms.

In viruses, NA exists as a tetramer made of four roughly spherical subunits and a centrally-attached stalk containing a hydrophobic region by which it is embedded in the organism's membrane. Several roles have been suggested for NA. The enzyme catalyzes cleavage of the α-ketosidic linkage between terminal sialic acid and an adjacent sugar residue. Removal of the sialic acid lowers the viscosity and permits access of the virus to the epithelial cells. NA also destroys the HA receptor on the host cell, thus allowing elution of progeny virus particles from infected cells.

Research indicates that the active site for influenza neuraminidase remains substantially unchanged for the major strains of influenza. For example, a comparison of sequences from influenza A subtypes and influenza B shows conserved residues with crucial structural and functional roles. Even though the sequence homology is only about 30%, many of the catalytic residues are conserved. Furthermore, the three-dimensional structures of influenza A and B neuraminidases have been determined. Superposition of the various structures shows remarkable structural similarity of the active site. Since the active site amino acid residues are conserved in all known influenza A neuraminidases that have been sequenced so far, an inhibitor that is effective against different strains of influenza A and/or B neuraminidase can be designed based on the three-dimensional structure of a neuraminidase.

In general, the role of NA is thought to be for the mobility of the virus both to and from the site of infections. Compounds that inhibit neuraminidase's activity may protect a subject from infection and/or cure a subject once infection has set in. It is a further object of this invention to provide a method of using compounds of this invention for treating and/or curing a viral infection.

Analogs of neuraminic acid, such as 2-deoxy-2,3-didehydro-N-acetylneuraminic acid (DANA) and its derivatives are known to inhibit NA in vitro; however, these compounds are inactive in vivo. Palese and Schulman, in CHEMOPROPHYLAXIS AND VIRUS INFECTION OF THE UPPER RESPIRATORY TRACT, Vol. 1 (J.S. Oxford, Ed.), CRC Press, 1977, at PS 189–205.

Von Itzstein et al. describes cyclohexane analogs of α-D-neuraminic acid of the formula

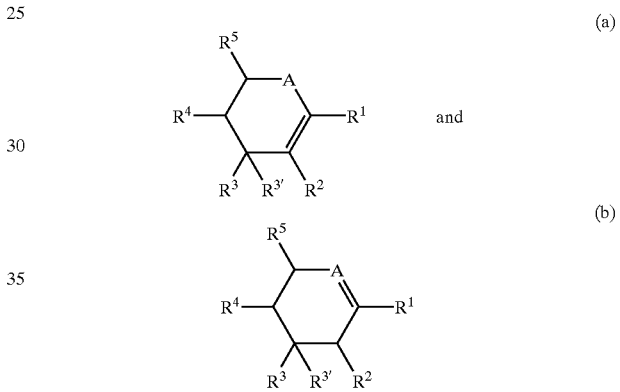

wherein:
A is, O, C or S in Formula (a), and N or C in Formula (b);
$R^1$ is $CO_2H$, $PO_3H_2$, $NO_2$, $SO_2H$, $SO_3H$, tetrazolyl-, $CH_2CHO$, CHO, or $CH(CHO)_2$;
$R^2$ is H, $OR^6$, F, Cl, Br, CN, $NHR^6$, $SR^6$ or $CH_2X$, where X is $NHR^6$ halogen, or $OR^6$;
$R^3$ and $R^3$, are H, CN, $NHR^6$, $SR^6$, $=NOR^6$, $OR^6$, guanidino, $NR^6$;
$R^4$ is $NHR^6$, $SR^6$, $OR^6$, $CO_2R^6$, $NO_2$, $C(R^6)_3$, $CH_2CO_2R^6$, $CH_2NO_2$ or $CH_2NHR^6$;
$R^5$ is $CH_2YR^6$, $CHYR^6CH_2YR^6$ or $CHYR^6CHYR^6CH_2YR^6$;
$R^6$ is H, acyl, alkyl, allyl, or aryl;
Y is O, S, NH, or H;
and pharmaceutical salts thereof, useful as antiviral agents.

In addition, certain benzene derivatives are suggested in U.S. Pat. No. 5,453,533 as being inhibitors of influenza virus neuraminidase and various others are disclosed in U.S. Pat. No. 5,602,277. Yamamoto et al. describe various sialic acid isomers as having inhibitory activity against neuraminidase in Synthesis of Sialic Acid Isomers With Inhibitory Activity Against Neuramninidase, TETRAHEDRON LETTERS, Vol. 33, No. 39, pp. 5791–5794, 1992.

WO 96/26933 to Gilead Sciences, Inc. describes certain 6-membered ring compounds as possible inhibitors of neuraminidase.

WO 98/17647 to Gilead Sciences, Inc. describes certain 6-membered piperidine compounds as possible inhibitors of neuraminidase.

Hoff et al suggest that certain N-aryl α-pyrrolidinones are useful as intermediates for dyes and pharmaceuticals, as reported in *Chemical Abstracts*, Vol. 52, Item 11124g, 1958.

However, none of these references disclose the pyrrolidine derivatives of the present invention.

SUMMARY OF INVENTION

The present invention relates to certain substituted pyrrolidine compounds. More particularly, the compounds of the present invention are selected from the group consisting of the following formulae:
wherein wherein Z is —C($R_2$)($R_3$), —CH—N($R_2$)($R_3$), C($R_3$)[(CH$_2$)n$R_2$], or CH—C($R_3$)(CH$_2$)n$R_2$;

$R_1$ is H, (CH$_2$)nOH, (CH$_2$)nNH$_2$, (CH$_2$)nNR$_{10}$R$_{11}$, (CH$_2$)nOR$_{11}$, or (CH$_2$)nF;

$R_9$ is (CH$_2$)nCO$_2$H, (CH$_2$)nSO$_3$H, (CH$_2$)nPO$_3$H$_2$, (CH$_2$)nNO$_2$, esters thereof, or salts thereof;

$R_2$ is H, NHC(O)$R_5$, NHC(S)$R_5$, NHSO$_2$R$_5$, C(O)NHR$_5$, SO$_2$NHR$_5$, CH$_2$S(O)R$_5$, or CH$_2$SO$_2$R$_5$;

$R_3$ is H, (CH$_2$)nCO$_2$R$_{10}$, (CH$_2$)mOR$_{10}$, C(O)N(R$_{10}$)m, (CH$_2$)nN(R$_{10}$)m, CH(R$_{10}$)m, (CH$_2$)n(R$_{10}$)m, CH$_2$CH(OR$_{10}$)CH$_2$OR$_{10}$, CH(OR$_{10}$)CH(OR$_{10}$)CH$_2$OR$_{10}$, CH$_2$OR$_{10}$, CH(OR$_{10}$)CH$_2$NHR$_{10}$, CH$_2$CH(OR$_{10}$)CH$_2$NHR$_{10}$, CH(OR$_{10}$)CH(OR$_{10}$)CH$_2$NHR$_{10}$, C(=NR$_{10}$)N(R$_{10}$)m, NHR$_{10}$, or NHC(=NR$_{10}$)N(R$_{10}$)m;

$R_4$ is H, (CH$_2$)nOH, (CH$_2$)nNR$_{10}$R$_{11}$, (CH$_2$)nNH$_2$, (CH$_2$)nC(=NH)(NH$_2$), (CH$_2$)nR$_{10}$R$_{11}$, (CH$_2$)nNHC(=NR$_{11}$)NH$_2$, (CH$_2$)nNHC(=NR$_7$)NH$_2$, (CH$_2$)nCN, (CH$_2$)nN$_3$, C(=NH)NH$_2$, C(NR$_7$)NH$_2$, or C(NR$_{11}$)NH$_2$;

$R_5$ is H, lower alkyl, lower branched chain alkyl, cyclic alkyl, halogen substituted alkyl, aryl, substituted aryl, or CF$_3$;

$R_7$ is H, (CH$_2$)nOH, (CH$_2$)nCN, (CH$_2$)nNH$_2$, or (CH$_2$)nNO$_2$;

$R_{10}$ is H, lower alkyl, lower alkylene, lower branched alkyl, cyclic alkyl, (CH$_2$)n aromatic, (CH$_2$)n substituted aromatic, or when m is 2 both $R_{10}$ groups can also be interconnected to form an N substituted heterocyclic ring, or other 5 or 6 membered heterocyclic ring;

$R_{11}$ is lower alkyl, lower branched alkyl, or (CH$_2$)m aromatic;

$R_{13}$ is H, (CH$_2$)nOH, (CH$_2$)nNH$_2$, (CH$_2$)nNR$_{10}$R$_{11}$, (CH$_2$)nOR$_{11}$, (CH$_2$)nF, (CH$_2$)nOC(O)R$_{11}$, or (CH$_2$)nNHC(O)R$_{11}$;

m is 1 or 2;

n is 0–4;

and pharmaceutically acceptable salts thereof.

The present invention is also concerned with compositions for inhibiting influenza virus neuraminidase comprising a pharmaceutically acceptable carrier and an amount effective for inhibiting influenza virus neuraminidase of a compound as defined above.

A further aspect of the present invention involves a method for inhibiting influenza virus that comprises administering to a patient in need thereof a compound as defined above in an amount effective for inhibiting influenza virus neuraminidase.

A still further aspect of the present invention is concerned with treating influenza virus infection comprising administering to a patient in need thereof a compound as defined above in an amount effective for inhibiting influenza virus neuraminidase.

The present invention is also concerned with methods for producing the compounds defined above.

BEST AND VARIOUS MODES FOR CARRYING OUT INVENTION

The present invention relates to certain pyrrolidine compounds. More especially, the compounds of the present invention are selected from the group consisting of the following formulae:

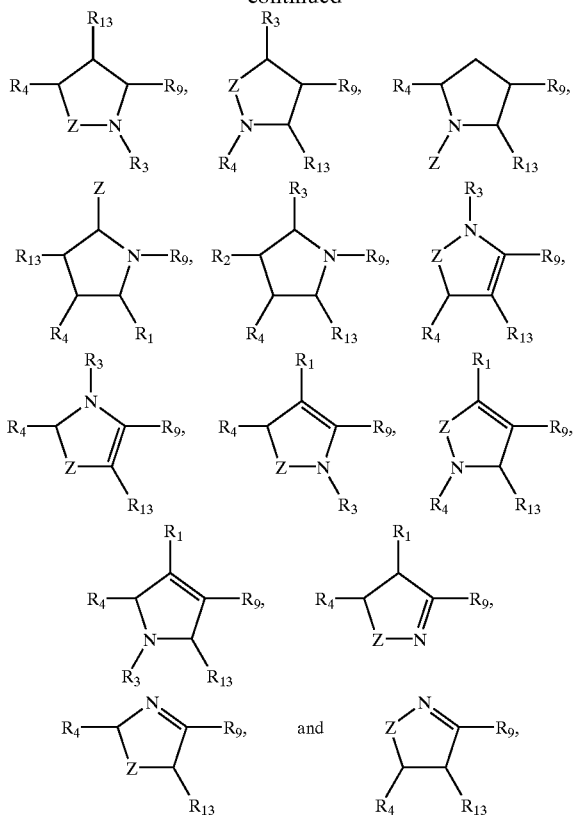

and pharmaceutically acceptable salts thereof; and wherein

Z is $-C(R_2)(R_3)$, $-CH-N(R_2)(R_3)$, $C(R_3)[(CH_2)nR_2]$, or $CH-C(R_3)(CH_2)nR_2$;

$R_1$ is H, $(CH_2)nOH$, $(CH_2)nNH_2$, $(CH_2)nNR_{10}R_{11}$, $(CH_2)nOR_{11}$, or $(CH_2)nF$;

$R_9$ is $(CH_2)nCO_2H$, $(CH_2)nSO_3H$, $(CH_2)nPO_3H_2$, $(CH_2)nNO_2$, esters thereof, or salts thereof;

$R_2$ is H, $NHC(O)R_5$, $NHC(S)R_5$, $NHSO_2R_5$, $C(O)NHR_5$, $SO_2NHR_5$, $CH_2S(O)R_5$, or $CH_2SO_2R_5$;

$R_3$ is H, $(CH_2)nCO_2R_{10}$, $(CH_2)mOR_{10}$, $C(O)N(R_{10})m$, $(CH_2)nN(R_{10})m$, $CH(R_{10})m$, $(CH_2)n(R_{10})m$, $CH_2CH(OR_{10})CH_2OR_{10}$, $CH(OR_{10})CH(OR_{10})CH2OR_{10}$, $CH_2OR_{10}$, $CH(OR_{10})CH_2NHR_{10}$, $CH_2CH(OR_{10})CH_2NHR_{10}$, $CH(OR_{10})CH(OR_{10})CH_2NHR_{10}$, $C(=NR_{10})N(R_{10})m$, $NHR_{10}$, or $NHC(=NR_{10})N(R_{10})m$;

$R_4$ is H, $(CH_2)nOH$, $(CH_2)nNR_{10}R_{11}$, $(CH_2)nNH_2$, $(CH_2)nC(=NH)(NH2)$, $(CH_2)nR_{10}R_{11}$, $(CH_2)nNHC(=NR_{11})NH_2$, $(CH_2)nNHC(=NR_7)NH_2$, $(CH_2)nCN$, $(CH_2)nN_3$, $C(=NH)NH_2$, $C(NR_7)NH_2$, or $C(NR_{11})NH_2$;

$R_5$ is H, lower alkyl, lower branched chain alkyl, cyclic alkyl, halogen substituted alkyl, aryl, substituted aryl, or $CF_3$;

$R_7$ is H, $(CH_2)nOH$, $(CH_2)nCN$, $(CH_2)nNH_2$, or $(CH_2)nNO_2$;

$R_{10}$ is H, lower alkyl, lower alkylene, lower branched alkyl, cyclic alkyl, $(CH_2)n$ aromatic, $(CH_2)n$ substituted aromatic, or when m is 2 both $R_{10}$ groups can also be interconnected to form an N substituted heterocyclic ring, or other 5 or 6 membered heterocyclic ring;

$R_{11}$ is lower alkyl, lower branched alkyl, or $(CH_2)m$ aromatic;

$R_{13}$ is H, $(CH_2)nOH$, $(CH_2)nNH_2$, $(CH_2)nNR_{10}R_{11}$, $(CH_2)nOR_{11}$, $(CH_2)nF$, $(CH_2)nOC(O)R_{11}$, or $(CH_2)nNHC(O)R_{11}$;

m is 1 or 2; and n is 0–4.

The esters are typically lower alkyl esters having 1 to about 12 carbon atoms and preferably 1 to about 3 carbon atoms and aryl esters containing 6 to 14 carbon atoms. The alkyl esters can be straight-chain, branched-chain or cyclic saturated aliphatic hydrocarbons.

Examples of some alkyl esters are methyl, ethyl, propyl, isopropyl, t-butyl, cyclopentyl and cyclohexyl esters. The aryl esters are preferably phenyl or alkyl substituted aromatic esters (alkaryl) including $C_{1-3}$ alkyl substituted phenyl such as benzyl.

The alkyl groups typically contain 1 to about 12 carbon, and preferably 1 to about 3 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. Examples of suitable cyclic aliphatic groups typically contain 3–8 carbon atoms and include cyclopentyl and cyclohexyl.

Examples of substituted cycloalkyl groups include cyclic aliphatic groups typically containing 3–8 carbon atoms in the ring substituted with alkyl groups typically having 1–6 carbon atoms and/or hydroxy group. Usually 1 or 2 substituted groups are present.

Examples of aryl groups are phenyl and naphthyl. Alkaryl groups typically contain 1–3 carbon atoms in the alkyl group such as benzyl. The alkyl moiety can be linear or branched.

Suitable heterocyclic rings include those containing N, 0 or S atoms and having 5 or 6 members in the ring. Examples include pyrrolidinyl, piperidinyl, morpholinyl, 2- and 3-thienyl, and 2-and 3-furanyl.

Pharmaceutically acceptable salts of the compounds of formula (I) include those derived from pharmaceutically acceptable, inorganic and organic acids and bases. Examples of suitable acids include hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic, trifluoroacetic and benzenesulphonic acids.

Salts derived from appropriate bases include alkali such as sodium and ammonia.

Examples of some specific compounds within the scope of the present invention are:

trans-3-Acetylamino-4-hydroxypyrrolidine-1-acetic acid;

cis-3-Acetylamino-4-hydroxypyrrolidine-1-acetic acid;

trans-3-Acetylamino-4-aminopyrrolidine-1-acetic acid;

trans-3-Acetylamino-4-(aminoiminomethyl) aminopyrrolidine-1-acetic acid;

cis-3-Acetylamino-4-(aminoiminomethyl) aminopyrrolidine-1-acetic acid;

trans-5-(1-Acetylamino-2-ethyl)butyl-1-aminoiminomethylpyrrolidine-3-carboxylic acid.

Compounds according to the present invention can be prepared according to the following schemes:

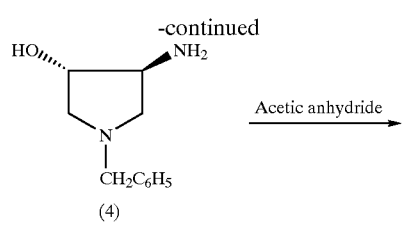

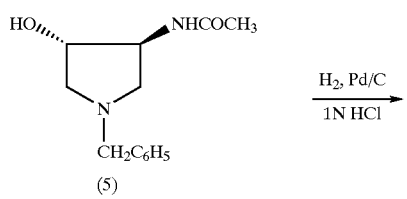

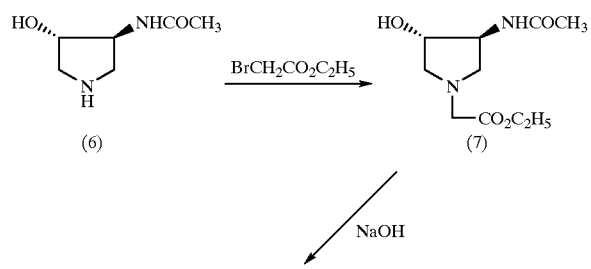

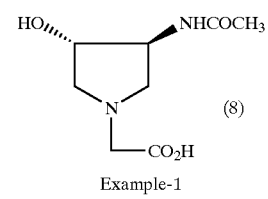

Scheme-1

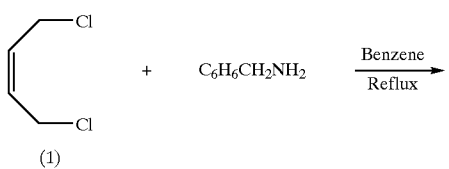

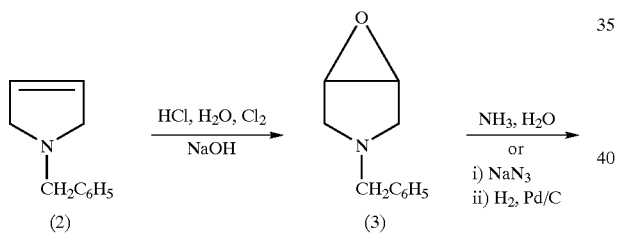

Scheme-2

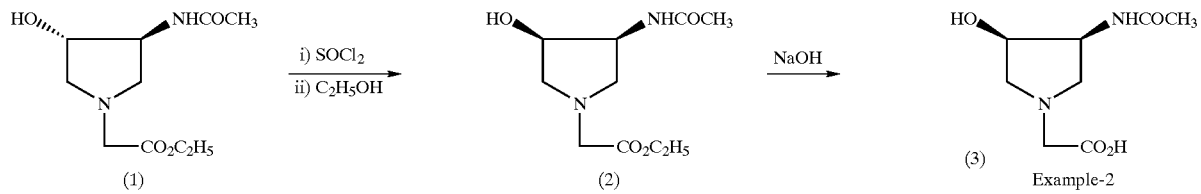

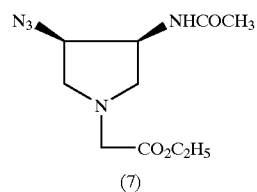
(7)
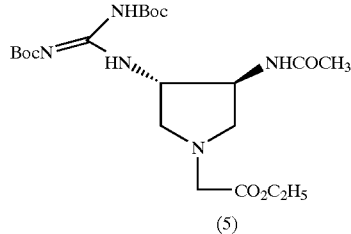
(5)
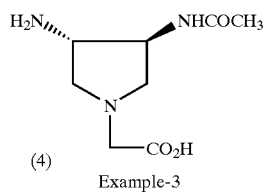
(4) Example-3
i) H₂, PtO₂
ii) Bis boc S-methyl isothiourea
iii) CF₃CO₂H
iv) NaOH
i) CF₃CO₂H
ii) NaOH
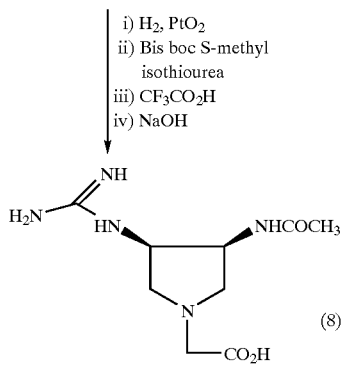
(8)
Example-5
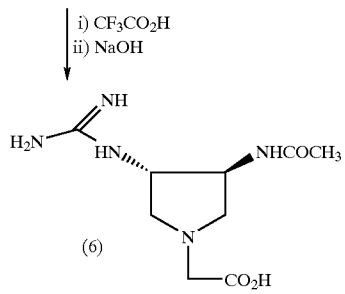
(6)
Example-4
Scheme-3
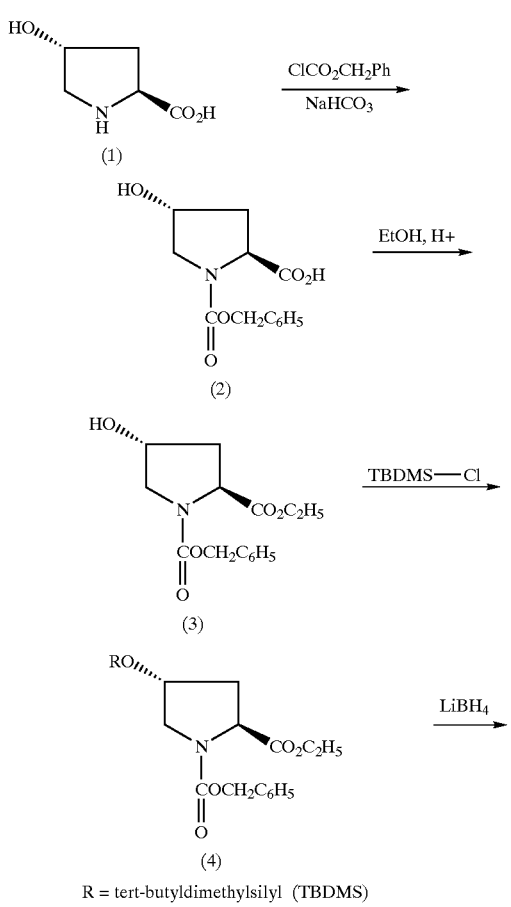
R = tert-butyldimethylsilyl (TBDMS)
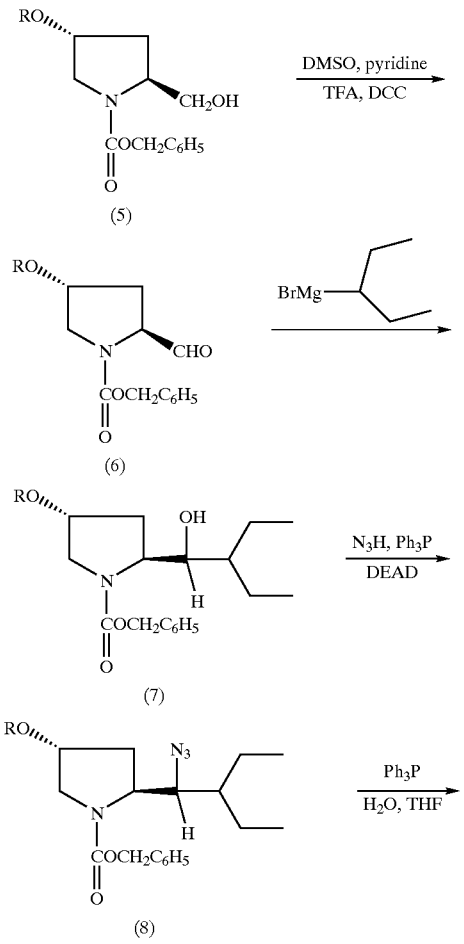

-continued
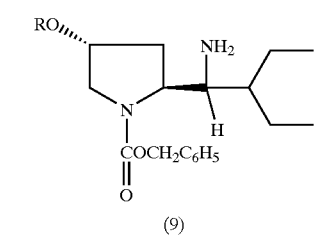
(9) → Ac₂O/DMAP
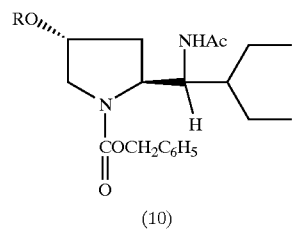
(10) → HCl, MeOH
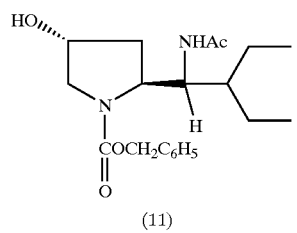
(11) → Ph₃P, AcOH, DEAD
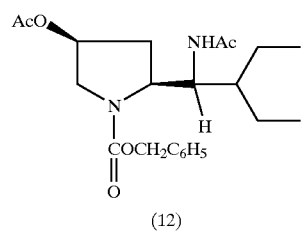
(12) → NH₄OH
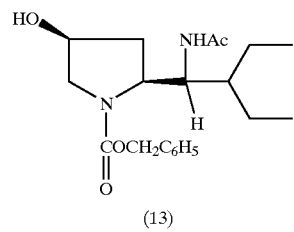
(13) → CH₃SO₂Cl
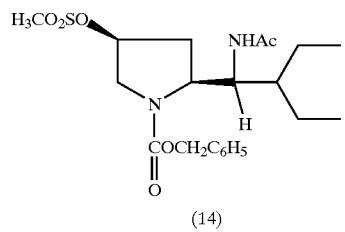
(14) → NaCN, DMSO
-continued
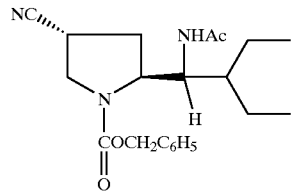
(15) → HCl, MeOH
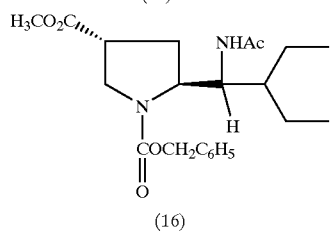
(16) → Pd/C, H₂
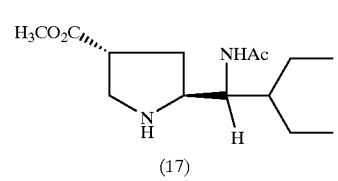
(17) → Bis Boc-S-methyl isothiourea
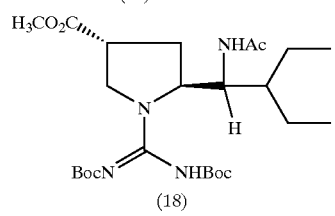
(18) → NaOH
Boc = tert-butoxycarbonyl
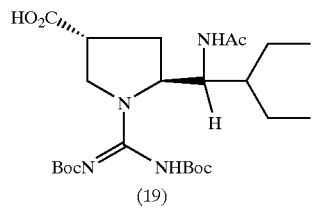
(19) → CF₃CO₂H
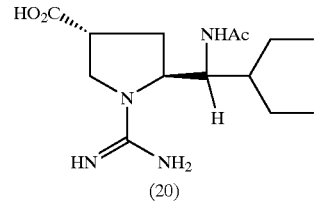
(20)
Example 6
Scheme-4
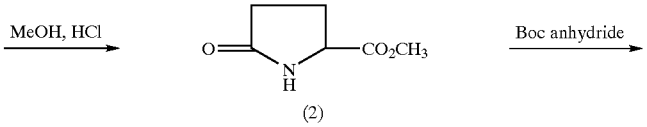
(1) → MeOH, HCl → (2) → Boc anhydride

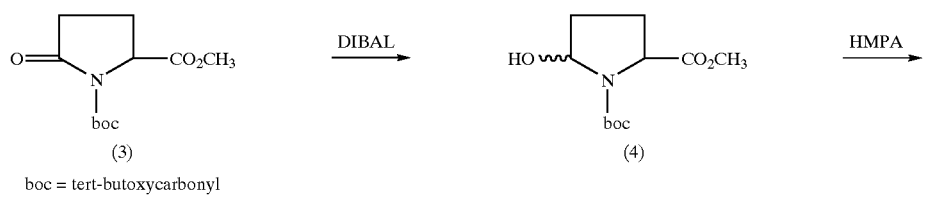
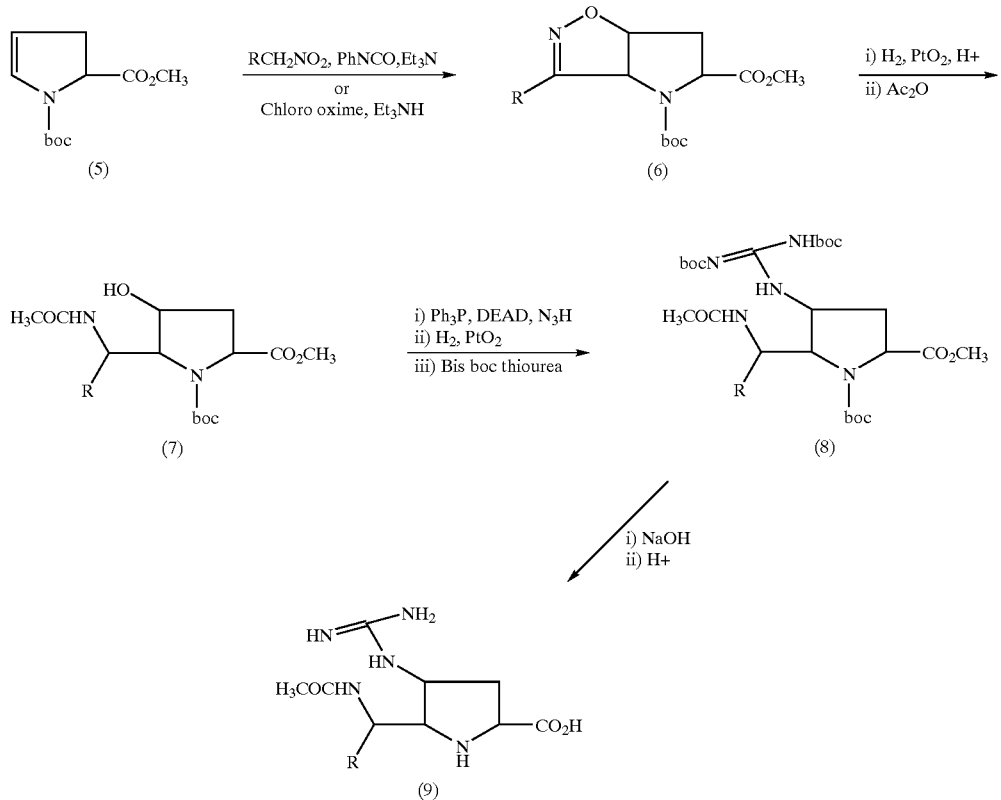
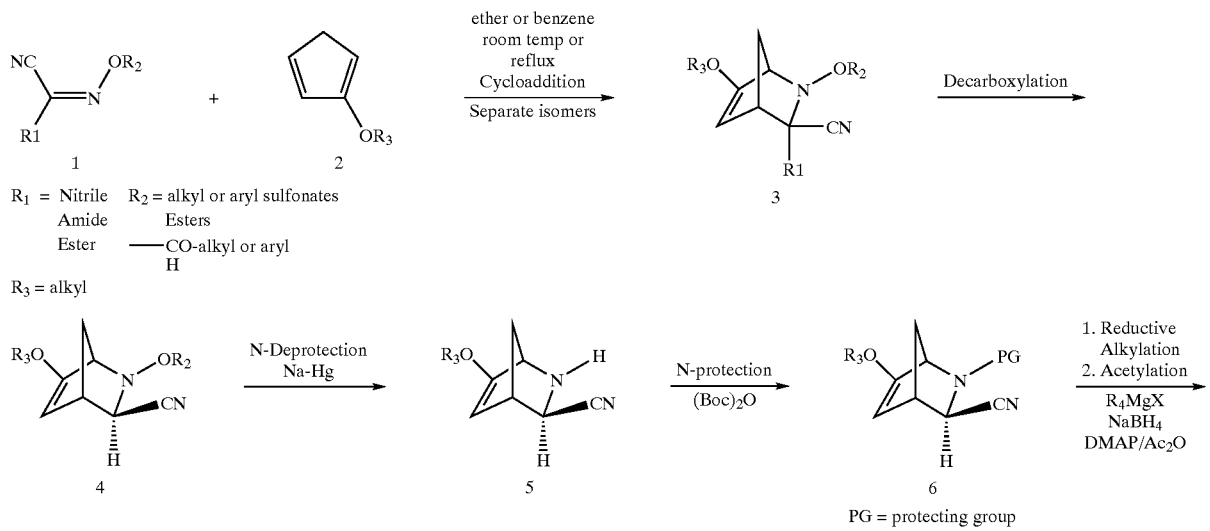

-continued

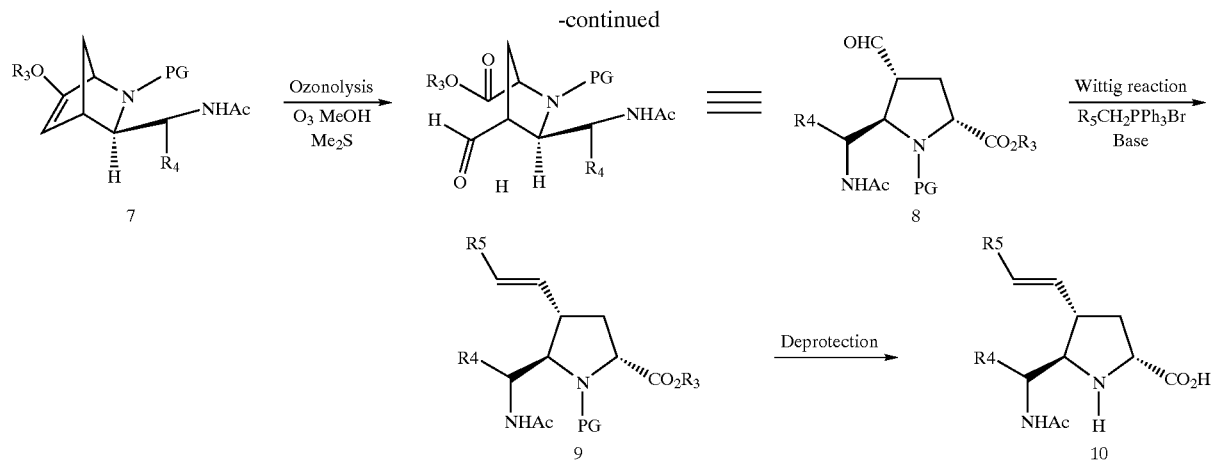

As shown in Scheme-5, the cycloaddition reaction of oximino compound 1 [Biehler, J. M; Perchais, J; Fleury, J. P. *Bull. Soc. Chim Fr* 1971, 7, 2711] with 2-alkoxy-1,3-cyclopentadiene 2 [Wolfgang, K.; Karin, L. *Chem. Ber.* 1981, 114(1), 400–404 and Mironov, V. A.; Luk'yanov, V. T.; Bernadskii, A, A. *Zh. Org. Khim.* 1984, 20(10), 69–80] furnishes the azabicyclic compound 3 [Biehler, J. M; Perchais, J; Fleury, J. P. *Bull. Soc. Chim Fr* 1971, 7, 2711; Biehler, J. M; Perchais, J; Fleury, J. P.; Regent, A. *Tetrahedron Lett.* 1968, 4277; Fleury, J. P.; Biehler, J. M; Desbois, M. *Tetrahedron Lett.* 1969, 4091.; Biehler, J. M.; Fluery, J. P. *J. Heterocycl. Chem.* 1971, 8, 431.; Biehler, J. M.; Fluery, J. P. *Tetrahedron.* 1971, 27, 3171.; Fluery, J. P. *Chemia.* 1977, 31, 143. and Fluery, J. P. Desbois, M.; See, J. *Bull. Soc. Chim. Fr.* II .1978, 147.] as a mixture of isomers. The required isomer is separated and subjected to decarboxylation when $R_1$ is an ester. When $R_1$ is nitrile the hydrolysis is followed by decarboxylation [Biehler, J. M.; Fluery, J. P. *Tetrahedron.* 1971, 27, 3171]. The exo and endo isomers of compound 4 are separated at this stage. The deprotection of tosyloxy group in compound 4 is achieved by Na-Hg reduction [Biehler, J. M.; Fluery, J. P. *Tetrahedron.* 1971, 27, 3171] followed by protection of nitrogen in the azabicyclic system compound 5 as a tert-butoxy carbamate to give compound 6. Reductive alkylation followed by acetylation [Effenberger, F.; Roos, J. *Tetrahedron Asym.* 2000, 11(5), 1085–1095] provides compound 7. The ozonoylsis [Schill G.; Priester, C.; Windhovel, U.; Fritz, H, *Tetrahedron* 1987, 43(16), 3765–3786] of compound 7 favors the oxidation to form ester and aldehyde in the required cis configuration in compound 8. The Wittig reaction of compound 8 with appropriate ylide provides the alkene 9, which on hydrolysis of protecting groups furnishes target compound 10. Aldehyde group of 8 may be converted to other groups also, such as, $CH_2OH$, $CH_2Oalkyl/alkenyl/alkynyl$, $CO_2H$, amides, etc. through the standard chemical transformation reactions.

Scheme-6

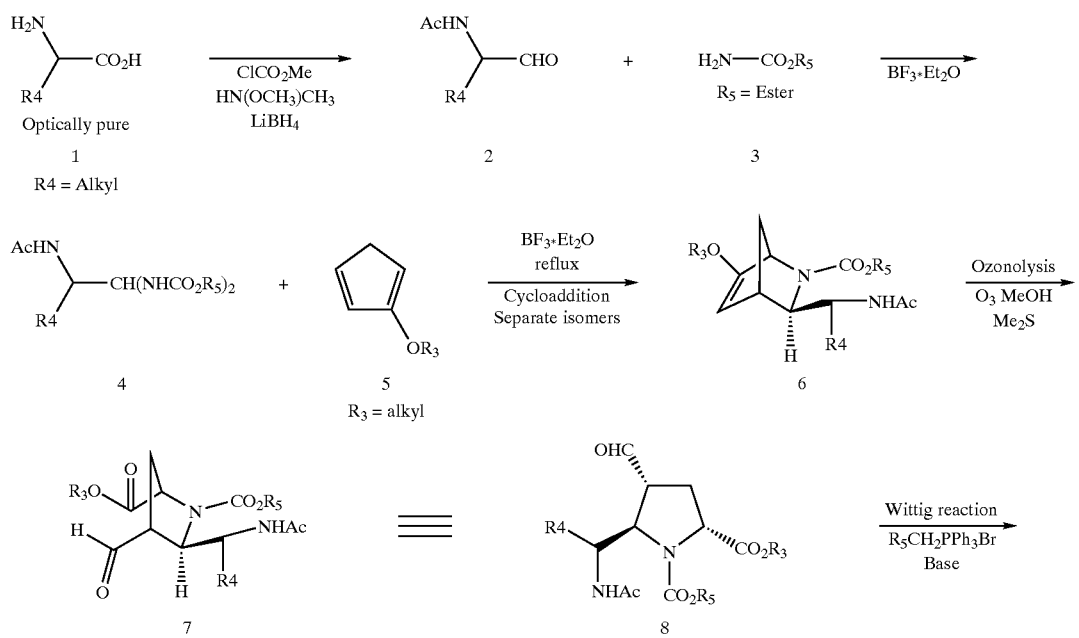

-continued

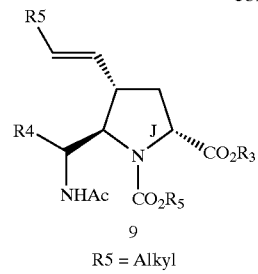

9
R5 = Alkyl

Deprotection →

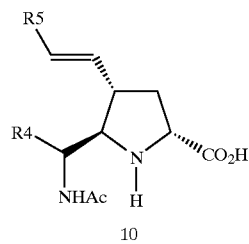

10

Scheme-6 takes the advantage of the availability of the optically pure alpha substituted amino acid 1 [Schollkopf, U.; Groth U.; Deng, C. *Angew. Chem. Int. Ed. Engl.* 1981, 20(11), 798–799. and Schollkopf, U.; Groth U. *Angew. Chem. Int. Ed. Engl.* 1981, 20(11), 977–978]. The chiral aldehyde 2 obtained from 1 is reacted with urethane 3 to form alkylidenebisurethanes 4, which undergo fragmentation in solution in presence of catalytic amounts of Lewis acid to afford dienophilic N-(alkoxycarbonyl)iminium ion [Sibi M. P. *Org. Prep. Proc. Int.* 1993, 25(1), 15–40 and Krow, G. R.; Henz, K. J.; Szczepanski, S. W. *J. Org. Chem.* 1985, 50, 1888–1894]. Thus 2-methoxy-1,3-cyclopentadiene 5 reacts with alkylidenebis(urethane) to furnish the azabicyclo compound 6 with preferential exo stereochemistry. The isomers are separated at this stage and the pure isomer is subjected to oxidation by ozonoylsis [Schill G.; Priester, C.; Windhovel, U.; Fritz, H, *Tetrahedron* 1987, 43(16), 3765–3786] to furnish compound 8 with the required cis stereochemistry. Further trasformations are the same as described in scheme-5.

The following non-limiting examples are presented to further illustrate the present invention.

EXAMPLE-1

Scheme-1 trans-3-Acetylamino-4-hydroxypyrrolidine-1-acetic Acid

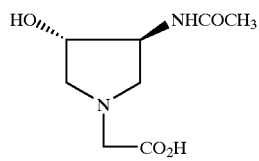

A mixture of 1,4-dichloro-cis-2-butene and benzylamine is heated at reflux to give 1-benzyl-3-pyrroline (2), which is converted to the epoxide (3) by first reacting (2) with chlorine in dilute hydrochloric acid and then with sodium hydroxide. The epoxide is opened to give the corresponding hydroxy amine (4) with either ammonia and water or sodium azide followed by reduction of the resulting azide. The resulting trans 1-benzyl-3-amino-4-hydroxypyrrolidine (4) is acetylated with acetic anhydride to give N-acetyl derivative (5) in which N-benzyl group is removed by hydrogenation in the presence of Pd/C under acidic conditions to give (6), and further alkylated with bromoethyl acetate to give N-ethoxycarbonyl methyl derivative (7). The basic hydrolysis of the ester (7) gives the target (8).

EXAMPLE-2

Scheme-2 cis-3-Acetylamino-4-hydroxypyrrolidine-1-acetic Acid

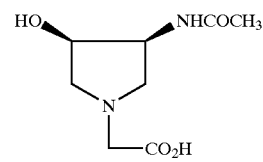

trans-3-Acetylamino-4-hydroxy-N-ethoxycarbonylmethylpyrrolidine (Scheme-1, No. 7) is converted to cis derivative (2) by reacting with thionyl chloride and ethanol. Basic hydrolysis of the ester gives the target (3).

EXAMPLE-3

Scheme-2 trans-3-Acetylamino-4-aminopyrrolidine-1-acetic Acid

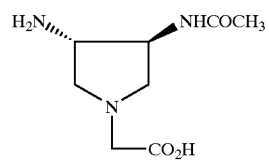

cis-3-Acetylamino-4-hydroxy-N-ethoxycarbonylmethylpyrrolidine (2) is reacted with hydrazoic acid, triphenylphosphine and diethyl azodicarboxylate (DEAD) to give the inverted azido derivative, which is further reduced to the amine by hydrogenation in the presence of PtO$_2$ and the ester is hydrolyzed with sodium hydroxide to give the target compound (4).

EXAMPLE-4

Scheme-2 trans-3-Acetylamino-4-(aminoiminomethyl) aminopyrrolidine-1-acetic Acid

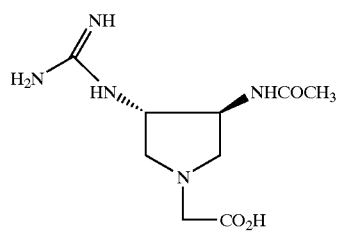

cis-3-Acetylamino-4-hydroxy-N-ethoxycarbonylmethylpyrrolidine (2) is reacted with hydrazoic acid, triphenylphosphine and diethyl azodicarboxylate (DEAD) to give the inverted azido derivative, which is further reduced to the amine by hydrogenation in the presence of $PtO_2$. The amine is converted to the bis boc protected guanidine derivative (5) with bis boa S-methylisothiourea in the presence of mercury (II) chloride and triethylamine. The hydrolysis of boa groups and ester with trifluoroacetic acid and sodium hydroxide gives the target compound (6).

EXAMPLE-5

Scheme 2 cis-3-Acetylamino-4-(aminoiminomethyl) aminopyrrolidine-1-acetic Acid

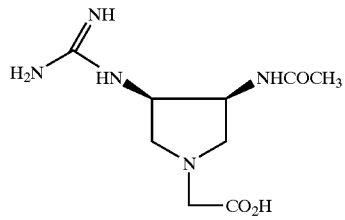

trans-3-Acetylamino-4-hydroxy-N-ethoxycarbonylmethylpyrrolidine (1, compound 7 from scheme-1) is reacted with hydrazoic acid, triphenylphosphine and diethyl azodicarboxylate (DEAD) to give the inverted azido derivative (7), which is further reduced to the amine by hydrogenation in the presence of $PtO_2$. The amine is converted to the bis boa protected guanidine derivative with bis boc S-methylisothiourea in the presence of mercury (II) chloride and triethylamine. The hydrolysis of boa groups and ester with trifluoroacetic acid and sodium hydroxide gives the target compound (8).

EXAMPLE-6

Scheme-3 trans-5-(1-Acetylamino-2-ethyl)butyl-1-aminoiminomethylpyrrolidine-3-carboxylic Acid

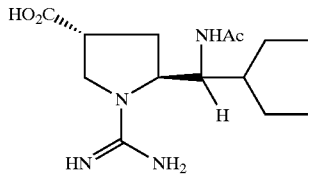

trans-4-Hydroxy-L-proline (Aldrich) is reacted with benzyl chloroformate to give N-benzyloxycarbonyl derivative (2), which is esterified with ethanol to give the corresponding ester (3). The hydroxyl group of (3) is protected with tert-butyldimethylsilyl group and the ester is reduced with lithium borohydride to give the alcohol (5). The oxidation of the alcohol to the aldehyde and the reaction of aldehyde with 2-ethyl-propyl magnesium bromide produced compound (7), which on reaction with hydrazoic acid, triphenylphosphine, and diethyl azodicarboxylate (DEAD) gives the azide (8). The reduction of azide with triphenylphosphine in THF and water gives the amine (9), which is acetylated to give the N-acetyl derivative (10), and the tert-butyldimethylsilyl group is removed under acidic conditions to give (11). The hydroxyl group of (11) is inverted with acetic acid, triphenylphosphine, and DEAD to give acetate (12), which is hydrolyzed with ammonium hydroxide to give the hydroxy compound (13). The compound (13) is reacted with methanesulfonyl chloride to give the mesylate (14), which is displaced with nitrile using sodium cyanide in DMSO to give (15), and hydrolysis of the nitrile under acidic conditions produces the ester (16). The deprotection of N-benzyloxycarbonyl group by hydrogenation in the presence of Pd/C gives (17), which is further converted with bis boc S-methylisothiourea to the protected amidine derivative (18). The deprotection of ester and boc groups with sodium hydroxide and trifluoroacetic acid yields the target composition (20).

Other isomers and derivatives of this type in the series may be prepared using the same methodology.

Scheme-4

Compounds of the type given in scheme-4 may be prepared as follows:

Compound (5), methyl N-(tert-butoxycarbonyl)-2-pyrroline-5-carboxylate is prepared by using the procedure of Dieter et al (*J. Org. Chem.* 1996, 61, 4180–4184). The reaction of compound (5) with appropriate nitroalkane, phenyl isocyanate, and triethylamine in toluene/benzene or with appropriate chloro oxime and triethylamine in THF/toluene gives the cycloadduct (6), which is further hydrogenated in the presence of a catalyst and the resultant amine is acetylated to give the N-acetyl derivative (7). The conversion of the hydroxyl group to the amine is achieved using the standard methods, and the amine is reacted with bis boc S-methylisothiourea to give the protected guanidine derivative (8). The hydrolysis of boc groups and the ester with trifluoroacetic acid and sodium hydroxide gives the target (9).

Dosage and Formulation

The antiviral compounds of this invention can be administered as treatment for viral infections by any means that produces contact of the active agent's site of action with the viral neuraminidase in the body of a human, mammal, bird, or other animal. They can be administered by an conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the preferred dose being 0.1 to about 30 mg/kg.

Dosage forms (compositions suitable for administration) contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation. Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company, a standard reference text in this field.

Useful pharmaceutical dosage forms for administration of the compounds according to the present invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mu of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Moreover, the compounds of the present invention can be administered in the form of nose drops or a nasal inhaler Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular. applications or uses of the invention. Accordingly, the description is not intended to limit the invention to the form disclosed herein. Also, it is intended that the appended claims be construed to include alternative embodiments.

What is claimed is:

1. Trans-5-(1-Acetylamino-2-ethyl)butyl-1-aminoiminomethylpyrrolidine-3-carboxylic acid.

\* \* \* \* \*